(12) United States Patent
Oliveti et al.

(10) Patent No.: US 11,596,309 B2
(45) Date of Patent: Mar. 7, 2023

(54) HYBRID MATCHING NETWORK TOPOLOGY

(71) Applicants:Anthony Oliveti, San Jose, CA (US); Tigran Poghosyan, San Jose, CA (US)

(72) Inventors: Anthony Oliveti, San Jose, CA (US); Tigran Poghosyan, San Jose, CA (US)

(73) Assignee: COMET TECHNOLOGIES USA, INC., San Jose, CA (US)

(*) Notice: Subject to any disclaimer, the term of this patent is extended or adjusted under 35 U.S.C. 154(b) by 6 days.

(21) Appl. No.: 17/458,786

(22) Filed: Aug. 27, 2021

(65) Prior Publication Data

US 2021/0386294 A1  Dec. 16, 2021
US 2022/0167851 A9  Jun. 2, 2022

Related U.S. Application Data

(62) Division of application No. 16/506,373, filed on Jul. 9, 2019, now Pat. No. 11,107,661.

(51) Int. Cl.
*A61B 5/00* (2006.01)
*A61B 34/32* (2016.01)
(Continued)

(52) U.S. Cl.
CPC .......... *A61B 5/0075* (2013.01); *A61B 5/0036* (2018.08); *A61B 5/0068* (2013.01);
(Continued)

(58) Field of Classification Search
None
See application file for complete search history.

(56) References Cited

U.S. PATENT DOCUMENTS 4,679,007 A  7/1987  Reese et al.
5,175,472 A  12/1992  Johnson, Jr. et al.
(Continued)

FOREIGN PATENT DOCUMENTS

JP  04239211 A  8/1992
JP  05284046 A  8/1993
(Continued)

OTHER PUBLICATIONS

PCT/US2018/062951—International Search Report and Written Opinion of International Searching Authority, dated Aug. 28, 2019, 10 pages.
(Continued)

*Primary Examiner* — Srinivas Sathiraju
(74) *Attorney, Agent, or Firm* — Nolte Lackenbach Siegel (57) ABSTRACT

The present disclosure relates to plasma generation systems which utilize plasma for semiconductor processing. The plasma generation system disclosed herein employs a hybrid matching network. The plasma generation system includes a RF generator and a matching network. The matching network includes a first-stage to perform low-Q impedance transformations during high-speed variations in impedance. The matching network includes a second-stage to perform impedance matching for high-Q impedance transformations. The matching network further includes a sensor coupled to the first-stage and the second-stage to calculate the signals that are used to engage the first and second-stages. The matching network includes a first-stage network that is agile enough to tune each state in a modulated RF waveform and a second-stage network to tune a single state in a RF modulated waveform. The plasma generation system also includes a plasma chamber coupled to the matching network.

20 Claims, 8 Drawing Sheets

(51) Int. Cl.
*G16H 20/40* (2018.01)
*A61B 18/22* (2006.01)
*A61B 18/20* (2006.01)
*A61B 17/00* (2006.01)
*A61B 18/00* (2006.01)

(52) U.S. Cl.
CPC .............. *A61B 5/444* (2013.01); *A61B 18/22* (2013.01); *A61B 34/32* (2016.02); *G16H 20/40* (2018.01); *A61B 2017/00761* (2013.01); *A61B 2018/00577* (2013.01); *A61B 2018/00642* (2013.01); *A61B 2018/20355* (2017.05)

(56) References Cited

U.S. PATENT DOCUMENTS

| | | |
|---|---|---|
| 5,195,045 A | 3/1993 | Keane et al. |
| 5,394,061 A | 2/1995 | Fujii |
| 5,474,648 A | 12/1995 | Patrick et al. |
| 5,576,629 A | 11/1996 | Turner et al. |
| 5,609,737 A | 3/1997 | Fukui et al. |
| 5,629,653 A | 5/1997 | Stimson |
| 5,737,175 A | 4/1998 | Grosshart et al. |
| 5,792,261 A | 8/1998 | Hama et al. |
| 5,810,963 A | 9/1998 | Tomioka |
| 5,842,154 A | 11/1998 | Harnett et al. |
| 5,849,136 A | 12/1998 | Mintz et al. |
| 5,866,869 A | 2/1999 | Schneider |
| 5,889,252 A | 3/1999 | Williams et al. |
| 5,910,886 A | 6/1999 | Coleman |
| 5,914,974 A | 6/1999 | Partlo |
| 6,016,131 A | 1/2000 | Sato et al. |
| 6,157,179 A | 12/2000 | Miermans |
| 6,164,241 A | 12/2000 | Chen et al. |
| 6,252,354 B1 | 6/2001 | Collins et al. |
| 6,313,584 B1 | 11/2001 | Johnson et al. |
| 6,313,587 B1 | 11/2001 | MacLennan et al. |
| 6,326,597 B1 | 12/2001 | Lubomirsky et al. |
| 6,407,648 B1 | 6/2002 | Johnson |
| 6,455,437 B1 | 9/2002 | Davidow et al. |
| 6,463,875 B1 | 10/2002 | Chen et al. |
| 6,507,155 B1 | 1/2003 | Barnes et al. |
| 6,677,828 B1 | 1/2004 | Harnett et al. |
| 6,703,080 B2 | 3/2004 | Reyzelman |
| 6,806,437 B2 | 10/2004 | Oh |
| 6,876,155 B2 | 4/2005 | Howald et al. |
| 6,894,245 B2 | 5/2005 | Hoffman |
| 6,949,887 B2 | 9/2005 | Kirkpatrick et al. |
| 7,030,335 B2 | 4/2006 | Hoffman |
| 7,042,311 B1 | 5/2006 | Hilliker et al. |
| 7,079,597 B1 | 7/2006 | Shiraishi et al. |
| 7,102,292 B2 | 9/2006 | Parsons et al. |
| 7,192,505 B2 | 3/2007 | Roche et al. |
| 7,196,283 B2 | 3/2007 | Buchberger, Jr. |
| 7,215,697 B2 | 5/2007 | Hill et al. |
| 7,220,937 B2 | 5/2007 | Hoffman |
| 7,251,121 B2 | 7/2007 | Bhutta |
| 7,259,623 B2 | 8/2007 | Coleman |
| 7,298,128 B2 | 11/2007 | Bhutta |
| 7,467,612 B2 | 12/2008 | Suckewer |
| 7,514,936 B2 | 4/2009 | Anwar |
| 7,795,877 B2 | 9/2010 | Radtke |
| 7,796,368 B2 | 9/2010 | Kotani |
| 7,800,368 B2 * | 9/2010 | Vaughan ............... G01R 33/246 324/318 |
| 8,169,162 B2 | 5/2012 | Yuzurihara |
| 8,203,372 B2 | 6/2012 | Arduini |
| 8,222,822 B2 | 7/2012 | Gilbert |
| 8,421,377 B2 | 4/2013 | Kirchmeier |
| 8,466,622 B2 | 6/2013 | Knaus |
| 8,471,746 B2 | 6/2013 | Kurunezi et al. |
| 8,491,759 B2 | 7/2013 | Pipitone et al. |
| 8,742,669 B2 | 6/2014 | Carter et al. |
| 8,779,662 B2 | 7/2014 | Boston |
| 8,803,424 B2 | 8/2014 | Boston |
| 8,884,180 B2 | 11/2014 | Ilie |
| 8,896,391 B2 | 11/2014 | du Toit |
| 8,928,229 B2 | 1/2015 | Boston |
| 9,042,121 B2 | 5/2015 | Walde et al. |
| 9,065,426 B2 | 6/2015 | Mason et al. |
| 9,105,447 B2 | 8/2015 | Brouk et al. |
| 9,111,725 B2 | 8/2015 | Boston |
| 9,124,248 B2 | 9/2015 | Van Zyl et al. |
| 9,142,388 B2 | 9/2015 | Hoffman et al. |
| 9,148,086 B2 | 9/2015 | Fife et al. |
| 9,166,481 B1 | 10/2015 | Vinciarelli |
| 9,171,700 B2 | 10/2015 | Gilmore |
| 9,196,459 B2 | 11/2015 | Bhutta |
| 9,208,992 B2 | 12/2015 | Brouk et al. |
| 9,224,579 B2 | 12/2015 | Finley et al. |
| 9,225,299 B2 | 12/2015 | Mueller et al. |
| 9,287,098 B2 | 3/2016 | Finley et al. |
| 9,294,100 B2 | 3/2016 | Van Zyl et al. |
| 9,306,533 B1 | 4/2016 | Mavretic |
| 9,313,870 B2 | 4/2016 | Walde et al. |
| 9,337,804 B2 | 5/2016 | Mason et al. |
| 9,345,122 B2 | 5/2016 | Bhutta |
| 9,385,021 B2 | 7/2016 | Chen |
| 9,418,822 B2 | 8/2016 | Kaneko |
| 9,478,397 B2 | 10/2016 | Blackburn et al. |
| 9,483,066 B2 | 11/2016 | Finley et al. |
| 9,490,353 B2 | 11/2016 | Van Zyl et al. |
| 9,496,122 B1 | 11/2016 | Bhutta |
| 9,520,269 B2 | 12/2016 | Finley et al. |
| 9,524,854 B2 | 12/2016 | Hoffman et al. |
| 9,525,412 B2 | 12/2016 | Mavretic |
| 9,536,713 B2 | 1/2017 | Van Zyl et al. |
| 9,543,122 B2 | 1/2017 | Bhutta |
| 9,544,987 B2 | 1/2017 | Mueller et al. |
| 9,558,917 B2 | 1/2017 | Finley et al. |
| 9,577,516 B1 | 2/2017 | Van Zyl et al. |
| 9,578,731 B2 | 2/2017 | Van Zyl |
| 9,584,090 B2 | 2/2017 | Mavretic |
| 9,589,767 B2 | 3/2017 | Hoffman et al. |
| 9,591,739 B2 | 3/2017 | Bhutta |
| 9,620,340 B2 | 4/2017 | Finley et al. |
| 9,651,957 B1 | 5/2017 | Finley et al. |
| 9,660,613 B2 | 5/2017 | Van Zyl et al. |
| 9,673,028 B2 | 6/2017 | Walde et al. |
| 9,697,911 B2 | 7/2017 | Bhutta |
| 9,711,331 B2 | 7/2017 | Mueller et al. |
| 9,711,335 B2 | 7/2017 | Christie et al. |
| 9,728,378 B2 | 8/2017 | Bhutta et al. |
| 9,729,122 B2 | 8/2017 | Mavretic |
| 9,741,544 B2 | 8/2017 | Van Zyl et al. |
| 9,745,660 B2 | 8/2017 | Bhutta |
| 9,748,076 B1 | 8/2017 | Choi et al. |
| 9,755,641 B1 | 9/2017 | Bhutta |
| 9,773,644 B2 | 9/2017 | Van Zyl et al. |
| 9,807,863 B1 | 10/2017 | Van Zyl et al. |
| 9,812,305 B2 | 11/2017 | Pelleymounter et al. |
| 9,844,127 B2 | 12/2017 | Bhutta |
| 9,852,890 B2 | 12/2017 | Mueller et al. |
| 9,854,659 B2 | 12/2017 | Van Zyl et al. |
| 9,865,432 B1 | 1/2018 | Bhutta |
| 9,952,297 B2 | 4/2018 | Wang |
| 10,008,317 B2 | 6/2018 | Iyer |
| 10,020,752 B1 | 7/2018 | Vinciarelli |
| 10,026,592 B2 | 7/2018 | Chen |
| 10,026,594 B2 | 7/2018 | Bhutta |
| 10,026,595 B2 | 7/2018 | Choi et al. |
| RE47,026 E * | 9/2018 | Vaughan ............ G01R 33/5612 |
| 10,074,518 B2 | 9/2018 | Van Zyl et al. |
| 10,139,285 B2 | 11/2018 | Murray et al. |
| 10,141,788 B2 | 11/2018 | Kamstedt |
| 10,194,518 B2 | 1/2019 | Van Zyl et al. |
| 10,217,618 B2 | 2/2019 | Larson et al. |
| 10,224,184 B2 | 3/2019 | Van Zyl et al. |
| 10,224,186 B2 | 3/2019 | Polak et al. |
| 10,263,577 B2 | 4/2019 | Van Zyl et al. |
| 10,269,540 B1 | 4/2019 | Carter et al. |
| 10,314,156 B2 | 6/2019 | Van Zyl et al. |
| 10,332,730 B2 | 6/2019 | Christie et al. |

(56) References Cited

U.S. PATENT DOCUMENTS

| | | | |
|---|---|---|---|
| 10,340,879 B2 | 7/2019 | Mavretic | |
| 10,373,811 B2 | 8/2019 | Christie et al. | |
| 10,374,070 B2 | 8/2019 | Wood | |
| 10,410,836 B2 | 9/2019 | McChesney | |
| 10,411,769 B2 | 9/2019 | Bae | |
| 10,447,174 B1 | 10/2019 | Porter, Jr. et al. | |
| 10,469,108 B2 | 11/2019 | Howald et al. | |
| 10,475,622 B2 | 11/2019 | Pankratz et al. | |
| 11,107,661 B2* | 8/2021 | Oliveti | H03H 7/40 |
| 2003/0121609 A1 | 7/2003 | Ohmi et al. | |
| 2003/0150710 A1 | 8/2003 | Evans et al. | |
| 2003/0230984 A1 | 12/2003 | Kitamura et al. | |
| 2004/0016402 A1 | 1/2004 | Walther et al. | |
| 2004/0026235 A1 | 2/2004 | Stowell, Jr. | |
| 2005/0034811 A1 | 2/2005 | Mahoney et al. | |
| 2005/0045475 A1 | 3/2005 | Watanabe | |
| 2005/0270805 A1 | 12/2005 | Yasumura | |
| 2006/0005928 A1 | 1/2006 | Howald | |
| 2006/0169582 A1 | 8/2006 | Brown et al. | |
| 2006/0169584 A1 | 8/2006 | Brown et al. | |
| 2006/0249729 A1 | 11/2006 | Mundt et al. | |
| 2007/0121267 A1 | 5/2007 | Kotani | |
| 2007/0222428 A1 | 9/2007 | Garvin et al. | |
| 2008/0061793 A1 | 3/2008 | Anwar et al. | |
| 2008/0061901 A1 | 3/2008 | Gilmore | |
| 2008/0087381 A1 | 4/2008 | Shannon et al. | |
| 2008/0129298 A1* | 6/2008 | Vaughan | G01R 33/583 324/322 |
| 2008/0197854 A1 | 8/2008 | Valcore et al. | |
| 2008/0272875 A1 | 11/2008 | Huang et al. | |
| 2008/0317974 A1 | 12/2008 | de Vries | |
| 2009/0026964 A1 | 1/2009 | Knaus | |
| 2009/0206974 A1 | 8/2009 | Meinke | |
| 2010/0012029 A1 | 1/2010 | Forester et al. | |
| 2010/0072172 A1 | 3/2010 | Ui et al. | |
| 2010/0096261 A1 | 4/2010 | Hoffman et al. | |
| 2010/0098882 A1 | 4/2010 | Lubomirsky et al. | |
| 2010/0159120 A1 | 6/2010 | Dzengeleski et al. | |
| 2011/0121735 A1 | 5/2011 | Penny | |
| 2011/0140607 A1 | 6/2011 | Moore et al. | |
| 2011/0148303 A1 | 6/2011 | Van Zyl et al. | |
| 2011/0174777 A1 | 7/2011 | Jensen et al. | |
| 2012/0097104 A1 | 4/2012 | Pipitone et al. | |
| 2012/0097524 A1 | 4/2012 | Pipitone et al. | |
| 2012/0145322 A1 | 6/2012 | Gushiken et al. | |
| 2012/0164834 A1 | 6/2012 | Jennings et al. | |
| 2012/0262064 A1 | 10/2012 | Nagarkatti et al. | |
| 2013/0002136 A1 | 1/2013 | Blackburn et al. | |
| 2013/0140984 A1 | 6/2013 | Hirayama | |
| 2013/0180964 A1 | 7/2013 | Ilic | |
| 2013/0214683 A1 | 8/2013 | Valcore et al. | |
| 2013/0240482 A1 | 9/2013 | Nam et al. | |
| 2013/0278140 A1 | 10/2013 | Mudunuri et al. | |
| 2013/0345847 A1 | 12/2013 | Valcore et al. | |
| 2014/0225504 A1 | 8/2014 | Kaneko | |
| 2014/0239813 A1 | 8/2014 | Van Zyl | |
| 2014/0265911 A1 | 9/2014 | Kamata et al. | |
| 2014/0328027 A1 | 11/2014 | Zhang et al. | |
| 2014/0367043 A1 | 12/2014 | Bishara et al. | |
| 2015/0002020 A1 | 1/2015 | Boston | |
| 2015/0115797 A1 | 4/2015 | Yuzurihara | |
| 2015/0150710 A1 | 6/2015 | Evans et al. | |
| 2015/0313000 A1 | 10/2015 | Thomas et al. | |
| 2016/0002020 A1 | 1/2016 | Orita | |
| 2016/0248396 A1 | 8/2016 | Mavretic | |
| 2016/0308560 A1 | 10/2016 | Howald et al. | |
| 2017/0018349 A1 | 1/2017 | Otsubo et al. | |
| 2017/0133886 A1 | 5/2017 | Kurs et al. | |
| 2017/0202591 A1* | 7/2017 | Shelton, IV | A61B 18/1445 |
| 2017/0338081 A1 | 11/2017 | Yamazawa | |
| 2017/0345620 A1 | 11/2017 | Coumou et al. | |
| 2018/0034446 A1 | 1/2018 | Wood | |
| 2018/0102238 A1 | 4/2018 | Gu et al. | |
| 2018/0261431 A1 | 9/2018 | Hammond, IV | |
| 2019/0172683 A1 | 6/2019 | Mavretic | |
| 2019/0199241 A1 | 6/2019 | Murakami et al. | |
| 2019/0385822 A1 | 12/2019 | Marakhtanov et al. | |
| 2021/0013009 A1* | 1/2021 | Oliveti | H03H 7/40 |
| 2021/0386294 A1* | 12/2021 | Oliveti | H01J 37/32183 |
| 2022/0076933 A1* | 3/2022 | Scullin | H01J 37/32935 |
| 2022/0157581 A1* | 5/2022 | Scullin | H01J 49/488 |
| 2022/0167851 A9* | 6/2022 | Oliveti | A61B 5/0068 |
| 2022/0270859 A1* | 8/2022 | Poghosyan | G01R 29/0878 |

FOREIGN PATENT DOCUMENTS

| | | | |
|---|---|---|---|
| JP | 2006-310245 A | 6/2008 | |
| JP | 2010-016124 A | 1/2010 | |
| JP | 2015-502213 A | 1/2015 | |
| KR | 10-2006-0067957 A | 6/2006 | |
| KR | 10-2014-0077866 A | 6/2014 | |
| KR | 10-2017-0127724 A | 11/2017 | |
| KR | 10-2018-0038596 A | 4/2018 | |
| WO | 2012054305 | 4/2012 | |
| WO | 2012054306 | 4/2012 | |
| WO | 2012054307 | 4/2012 | |
| WO | 2016048449 A1 | 3/2016 | |
| WO | 2016097730 | 6/2016 | |
| WO | 2019096564 A1 | 5/2019 | |
| WO | 2019147513 A1 | 8/2019 | |
| WO | 2019-244734 A1 | 12/2019 | |

OTHER PUBLICATIONS

Stowell, et al., "RF-superimposed DC and pulsed DC sputtering for deposition of transparent conductive oxides", Thin Solid Films 515 (2007), pp. 7654-7657.

Bender, et al., "Characterization of a RF=dc-magnetron discharge for the sputter deposition of transparent and highly conductive ITO films", Appl. Phys. A 69, (1999), pp. 397-409.

Economou, Demetre J., "Fundamentals and application of ion-ion plasmas", Applied Surface Science 253 (2007), pp. 6672-6680.

Godyak et al., "Plasma parameter evolution in a periodically pulsed ICP", XXVIIth, Eindhoven, the Netherlands, Jul. 18-22, 2005, 4 pages.

Banna, et al., "Inductively Coupled Pulsed Plasmas in the Presence of Synchronous Pulsed Substrate Bias for Robust, Reliable, and Fine Conductor Etching", IEEE Transactions on Plasma Science, vol. 37, No. 9, Sep. 2009, pp. 1730-1746.

Kushner, Mark J., "Pulsed Plasmas as a Method to Improve Uniformity During Materials Processing", Journal of Applied Physics, Jul. 1, 2004, vol. 96, No. 1, pp. 82-93.

LTM Technologies, M. Haass "Synchronous Plasma Pulsing for Etch Applications", Apr. 3, 2010 16 pages.

PCT/US2020/038892—International Search Report and Written Opinion of the International Searching Authority, dated Oct. 6, 2020, 3 pages.

PCT/US2020/038899—International Search Report and Written Opinion of the International Searching Authority, dated Sep. 26, 2019, 5 pages.

PCT/US2021/012847—International Search Report and Written Opinion of the International Searching Authority, dated May 6, 2021, 11 pages.

PCT/US2021/012849 International Search Report and Written Opinion of the International Searching Authority, dated May 10, 2021, 11 pages.

PCT/US2021/012851 International Search Report and Written Opinion of the International Searching Authority, dated May 6, 2021, 10 pages.

* cited by examiner

HYBRID MATCHING NETWORK TOPOLOGY

CROSS-REFERENCE TO RELATED APPLICATIONS

This Application is a divisional application of, incorporates by reference, and claims priority to co-pending U.S. patent application Ser. No. 16/854,022 having the same inventorship and title as the instant application, which is incorporated by reference herein for all applicable purposes.

BACKGROUND

In semiconductor manufacturing, plasma processing chambers utilize radio frequency ("RF") power to generate plasma. Plasma is typically created and maintained by an electric current alternating at an RF frequency, which excites and ionizes the source gas used in the plasma chamber. Plasma processing chambers may be used for industrial processes such as, but not limited to, surface treatment of materials or plasma etching during a semiconductor fabrication process. To achieve efficient power transfer between a RF generator and a plasma load, an impedance-matching network is generally used to match a load impedance to a source impedance (e.g., 50 Ohms).

The plasma chamber presents electrical impedance that may vary greatly and quickly. It is important that the output impedance of the RF power generator be closely matched to the rapidly-changing load impedance of the plasma chamber to avoid damaging reflections of power back into the output circuitry of the RF power generator, which can occur when the impedances are mismatched. Impedance matching devices (e.g., matching networks) are used to match the load impedance of the plasma processing chamber to the output impedance of the RF power generator. For rapidly-varying load impedance, the matching network has to dynamically match the impedance accordingly.

BRIEF DESCRIPTION OF THE DRAWINGS

For a more complete understanding of the present disclosure, examples in accordance with the various features described herein may be more readily understood with reference to the following detailed description taken in conjunction with the accompanying drawings, where like reference numerals designate like structural elements.

DETAILED DESCRIPTION

The description of the different advantageous implementations has been presented for purposes of illustration and is not intended to be exhaustive or limited to the implementations in the form disclosed. Many modifications and variations will be apparent to a person having ordinary skill in the art. Further, implementations may provide different advantages as compared to other implementations. The implementation or implementations selected are chosen and described to best explain the principles of the implementations, the practical application, and to enable a person having ordinary skill in the art to understand the disclosure for various implementations with various modifications as are suited to the particular use contemplated.

Before the present disclosure is described in detail, it is to be understood that, unless otherwise indicated, this disclosure is not limited to specific procedures or articles, whether described or not. It is further to be understood that the terminology used herein is for the purpose of describing particular implementations only and is not intended to limit the scope of the present disclosure.

During plasma processing, a radio frequency ("RF") generator transmits RF alternating current ("AC") waves through RF transmission lines and networks to a plasma processing chamber. To provide an efficient transfer of power from the RF generator to the plasma processing chamber, a matching network is employed to transform the time-varying impedance presented by the plasma chamber to the optimal load impedance of the RF generator.

Many RF matching networks have variable capacitors and a control circuit with a microprocessor to control the capacitance values of the variable capacitors. There may be various configurations of RF matching networks. Herein, a vacuum variable capacitor may be defined as an electro-mechanical device which has two concentric metallic rings that are moved in relation to each other to change capacitance. The value and size of the variable capacitors within the RF matching network may be determined by the power handling capability, frequency of operation, and impedance range of the plasma processing chamber.

Pulse-Frequency Modulation is a commonly used technique to deliver power in plasma processing systems. Herein, Pulse-Frequency Modulation Is a modulation method where the amplitude of the carrier waveform is varied between at least two discrete power levels at some frequency with some duty cycle. As such, power delivered in a pulse-waveform may affect plasma characteristics which may therefore cause the electrical impedance of the plasma chamber to vary with each pulse waveform. At the onset of each pulse, a spike in reflected power can result.

Many RF plasma generation systems employ multi-level pulsing for various different power states. Each power state may be associated with a unique impedance because the characteristics of the plasma may change based on the delivered power to the plasma chamber. During plasma processing, the plasma changes occur very quickly (e.g., at a rate of up to hundreds of thousands of Hertz). Many matching networks, such as those that have vacuum variable capacitors, generally react on the order of hundreds or thousands of milliseconds.

Accordingly, many of these matching networks are limited to latching on to one of the multi-level power states (e.g., high or low amplitudes). For example, for dual level pulsing, a matching network may latch on to the high amplitude or to the lower amplitude state and maintain position for the duration of the other state. This means that the system will behave optimally during one state, and sub-optimally for any other states.

The present disclosure provides a mechanism to match to all states by reacting to all impedance states to maintain a low-reflection coefficient during impedance variations. Advantageously, the present disclosure reduces the tuning time in matching networks. Herein, tuning time is defined as the amount of time that it takes for a matching network system to reach a tuned state from a detuned state.

Figure 1:
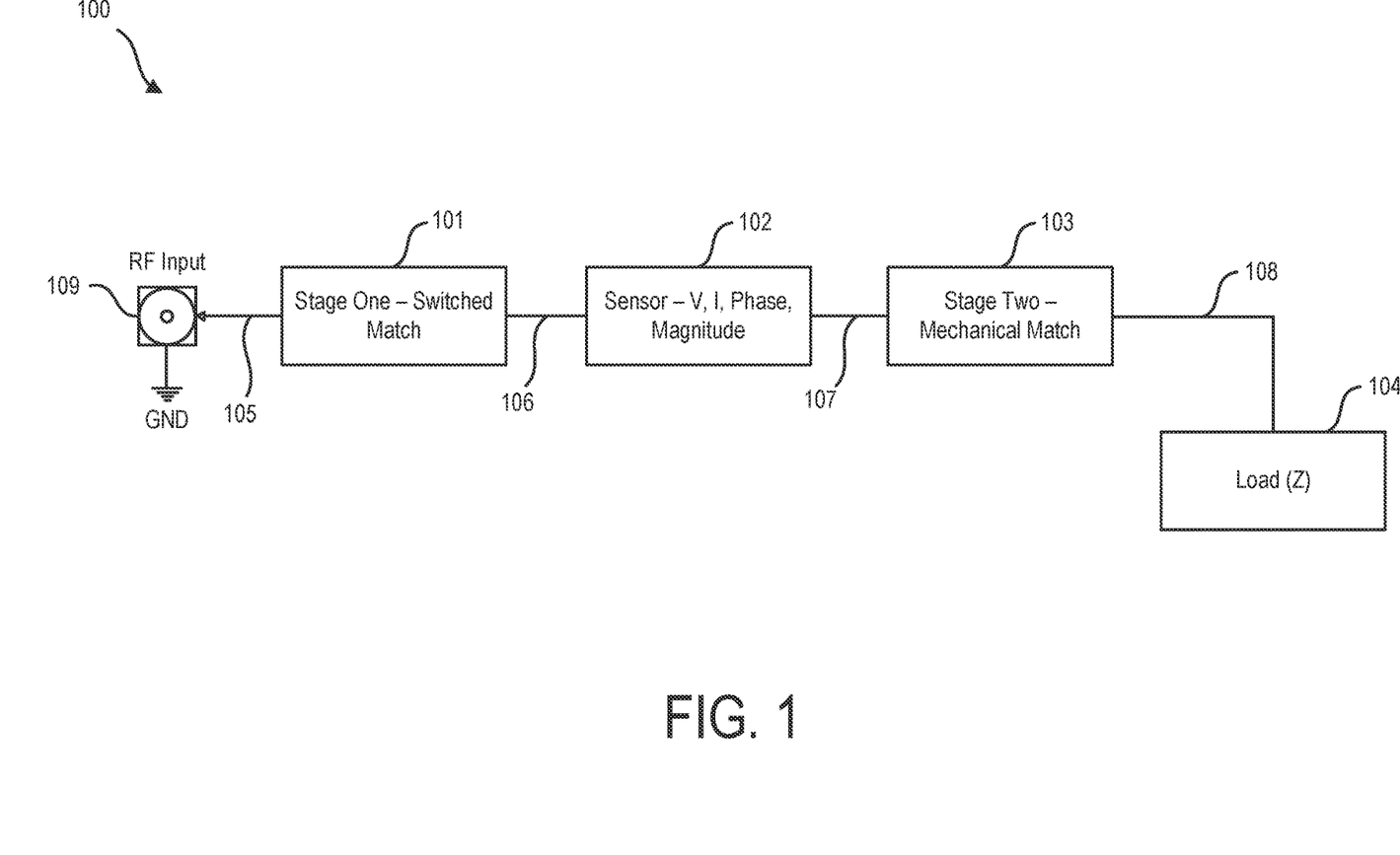
FIG. 1 is a block diagram of a hybrid matching network, according to a system and method of the present disclosure.

FIG. 1 is a block diagram of a hybrid matching network 100, according to a system and method of the present disclosure. Advantageously, the hybrid matching network 100 disclosed herein employs a two-stage tunable matching network. As shown, the hybrid matching network 100 receives its RF input from a RF generator at RF input 109, the first-stage matching network 101 (e.g., a switch network), the second-stage matching network 103 (e.g., a mechanically-tuned matching network), a sensor element 102, and plasma chamber 104 (e.g., load) which are all coupled to one or more transmission lines 105-108. Herein, a hybrid matching network 100 may be defined as a multi-stage matching network which can operate simultaneously or in sequence to tune a load impedance to a target (e.g., source) impedance.

The first-stage matching network 101 may be responsible for matching to high-speed variations in impedance during different stages of a RF waveform and a second-stage matching network 103 may be responsible for high-Q impedance transformations. Accordingly, in several implementations of the present disclosure, the bulk of the impedance tuning is performed by the second-stage matching network 103, for high-Q transformations and the first-stage matching network 101 can be used to tune system impedance for low-Q transformations that arise from a pulsed waveform, changes in chamber conditions, or other factors. Herein, high-speed variation is defined as a change in impedance that is beyond the control loop bandwidth associated with a second-stage matching network.

The first-stage matching network may include fixed capacitors and PIN diodes, silicon-carbide field effect transistors (SiCFETs), metal oxide field effect transistors (MOSFETs), insulated gate bipolar transistors (IGBTs), or bipolar junction transistors (BJTs) electronic switches and the second-stage matching network may include vacuum variable capacitors, or air variable capacitors, and stepper motors, brushed direct current (DC) motors, brushless DC motors, or AC motors.

Advantageously, the hybrid matching system as disclosed herein can reduce the stress on the high-speed, secondary matching network (e.g., the first-stage matching network 103) and can assist in dialing in the matching network to tune the plasma system to a target impedance.

Herein, high Q or low Q refers to a high or low-quality factor. The Q-factor is defined as the ratio of energy stored in a system to the amount of energy dissipated in a system. Q-factor is a dimensionless unit and, for a single element, is expressed as the ratio between the element's reactance and its resistance. In a matching network, the minimum Q-factor is the configuration where the least amount of energy is stored for the transformation to be accomplished.

In some implementations, a high-Q impedance transformation is one that has a Q-factor that is greater than two whereas a low-Q impedance transformation is one that has a Q-factor that is less than two.

Figure 2:
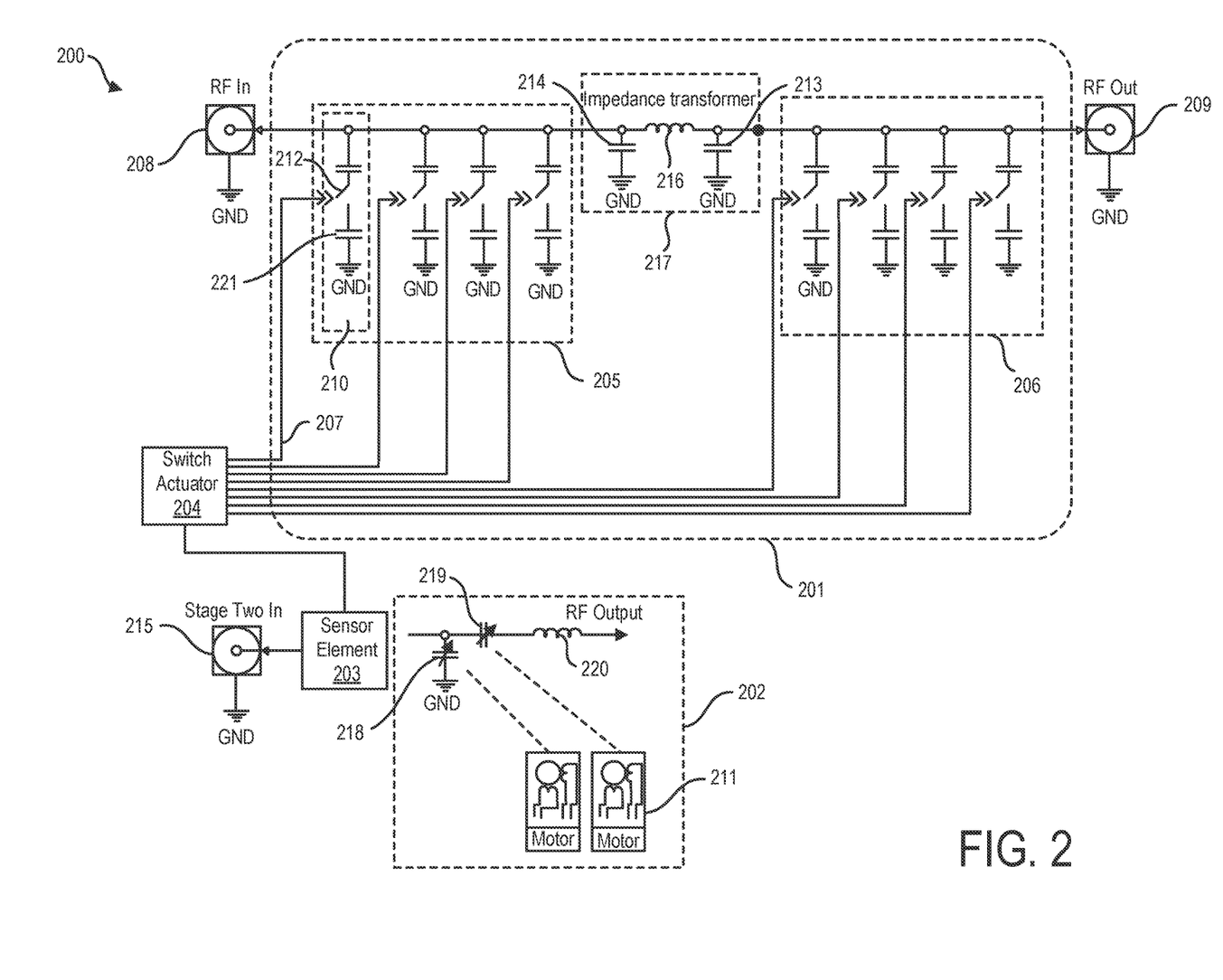
FIG. 2 is an illustration of a hybrid matching network topology, according to a system and method of the present disclosure.

FIG. 2 is an illustration of a hybrid matching network 200 topology, according to a system and method of the present disclosure. The hybrid matching network 200 topology illustrates a first-stage matching network 201, a second-stage matching network 202, and a sensor element 203 coupled thereto. In some implementations, the bulk of the tuning is performed by the second-stage matching network 202 whereas the first-stage matching network 201 can be employed to implement "coarse tuning" for low-level and fast impedance variations.

The voltage and current sensed at an output (e.g., node 209/215) of the first-stage matching network 201 can be used to direct both stages simultaneously as they act independently. The RF power is delivered by a RF generator to the system input node 208, which is delivered to a plasma chamber (not shown) by way of the hybrid matching network 200.

In the implementation shown, the first-stage matching network 201 includes an impedance transformer 217 with banks 205, 206 of switch terminals 210 (e.g., switched capacitors) on two sides of the impedance transformer 217. Collectively, the impedance transformer 217 and the banks 205, 206 of switch terminals 210 (e.g., switched capacitors) provide the first-stage matching network 201 the flexibility to match impedances, within a specified range. The impedance transformer 217 may include a lumped-element pi network or a distributed network such as a transmission line to achieve the desired impedance transformation. For example, the impedance transformer 217 may include a pi network section to perform both a step-up and step-down impedance transformation to tune to a target impedance.

The specified range of the first stage is a design choice which can be made based on the application and the availability of devices at a given frequency and power level. Choosing a narrow range may limit stress on the first stage for a given frequency and power level, but also limits the applications in which it may be used. Choosing a large range has the opposite consequence. In either case, the system may function similarly.

Accordingly, the present disclosure provides an impedance transformer 217 to be used in conjunction with banks 205, 206 of switch terminals 210 (e.g., switched capacitors) to tune an impedance. The impedance transformer 217 may be realized by inserting a section of a transmission line with appropriate electrical length and characteristic impedance. For example, a quarter-wave impedance transformer may be used to match real impedances. However, a complex load impedance can also be transformed to a real impedance by adding a series or shunt reactive component. Notably, a quarter-wave transformer can provide a match at a particular operating frequency as well as an acceptable match across a bandwidth of one octave, or less, depending on the quality factor, Q, of the transformation and the application.

In the implementation shown in FIG. 2, the impedance transformer 217 includes a lumped-element pi network. The impedance transformer 217 performs the same impedance transformation as the transmission line or waveguide and can be made much more compact at lower frequencies but offers a more limited bandwidth. In one implementation, the impedance transformer 217 of lumped elements consists of capacitors 213, 214 in shunt network branches in addition to an inductor 216 in a series branch.

The banks 205, 206 of switches 212 each include individual (e.g., RF) switch terminal 210 (in each respective banks 205, 206 of switches 212) which include switches 212 and reactive tuning elements 221 which allow the first stage to match a variety of load impedances. In some implementations, a look-up table stored in a memory element (not shown) of the hybrid matching network 200 may be referenced to determine the state of the switches 212 to collectively tune the output impedance of the first stage to a complex conjugate of the calculated input impedance of the second-stage matching network. In the implementation shown in FIG. 2, the banks 205, 206 each include four switch terminals 210 of switches 212 and therefore eight switch terminals 210 to effect impedance tuning. As will be described in more detail with respect to FIGS. 3 and 4, the number of switch terminals 210 can affect the tuning precision of the first-stage matching network 201.

In addition, a switch actuator 204 is coupled to each switch terminal 210 for each bank 205, 206 of switch terminals 210. Herein, a switch actuator is defined as the portion of the system responsible for bringing a switch terminal 210 into, or out of, the circuit by engaging (e.g. close) or disengaging (e.g. open) the switch 212 in that switch terminal 210. The switch actuator 204 may be coupled to the banks 205, 206 of switch terminals 210 by electrical, magnetic, optical, or mechanical means. In the implementation shown, the switch actuator 204 is coupled to the eight switches 212 in the banks 205, 206 of switch terminals 210. In addition, the switch actuator 204 is coupled to the sensor element 203. The sensor element 203 may operate the switch actuator 204 to engage the first-stage matching network 201.

The state of the switches 212 of the banks 205, 206 of switch terminals 210 may be expressed in a binary format. For example, a first-stage matching network 201 with the switches 212 of bank 205 all being closed and the switches 212 of bank 206 being open may be expressed as [1111 0000]. Likewise, a first-stage matching network 201 with the first half of the switches 212 of banks 205, 206 being open and the second half of the switches 212 of banks 205, 206 being closed may be expressed as [0011 0011]. In one implementation, a look-up table may be used to relate the proper configuration states of the switch terminals 210 to the readings from sensor element 203. In this case, after sensor data has been received and processed, the switch terminals 210 can be actuated to a set of states that minimizes the reflection coefficient (e.g. gamma) at the input 208 of the first stage.

The sensor element 203, as shown, is coupled to an input 215 of the second-stage matching network 202. The sensor element 203 can detect voltage and current, or forward and reflected coupled waves. The sensor element 203 may be a voltage and current sensor, or a bi-directional coupler which detects the voltage, current, forward, or reflected waveforms. In particular, the sensor element 203 measures voltage and current and calculates the relationship between the measured voltage and current in both phase and magnitude. Moreover, the sensor element 203 can detect high-speed variations in plasma chamber impedance and can use the change in impedance caused by the high-speed variations to engage the first-stage matching network 201.

It should be understood by a person having ordinary skill in the art having the benefit of this disclosure that the magnitude ratio and phase relationship of voltage and current waveforms at a particular node in a matching network can be used to direct the tunable elements in an automatic matching network. In this case, a notable aspect is the location of the sensor, and the types of information it gathers. The magnitude ratio and phase relationship of these quantities at the node where sensor element 203 exists in the system allow us to drive the second-stage matching network matching network as well as actuate the switch terminals 210 in the first-stage matching network simultaneously. In this implementation, magnitude and phase are used to drive the tunable elements in the second-stage matching network matching network, and those same values are used to calculate the input impedance to the second-stage matching network, which is the load impedance for the first-stage matching network. When this impedance is computed, the switch terminals 210 are actuated such that the output impedance of the first stage is the complex conjugate of the calculated load impedance. These operations occur simultaneously and independently. As the second-stage matching network self-adjusts its tunable elements to achieve a minimization of gamma looking into its input 215, it is constantly presenting some load at the input to the first stage. Therefore, under any circumstance where the impedance looking into node 215 is approximately the complex conjugate of one of the available configurations of switch terminals 210, the first stage can minimize gamma looking into node 208, which is the input to the hybrid matching system. As the second-stage matching network continuously drives towards minimum gamma at node 215, the first stage can continue to actuate switch terminals 210 to maintain the most optimal impedance match at node 208.

FIG. 2 also shows an illustration of the second-stage matching network 202. In some implementations, the second-stage matching network 202 may be configured similarly to conventional matching networks. For instance, the second-stage matching network 202 may include one or more variable capacitors 218, 219 and an inductor 220. The variable capacitors 218, 219 may be adjusted, for example, by a lead screw (not shown) in a mechanical means (e.g., using motors 211) to transform the impedance presented by a plasma chamber (not shown) to match a target impedance (e.g., source impedance, typically 50 ohms).

Figure 3:
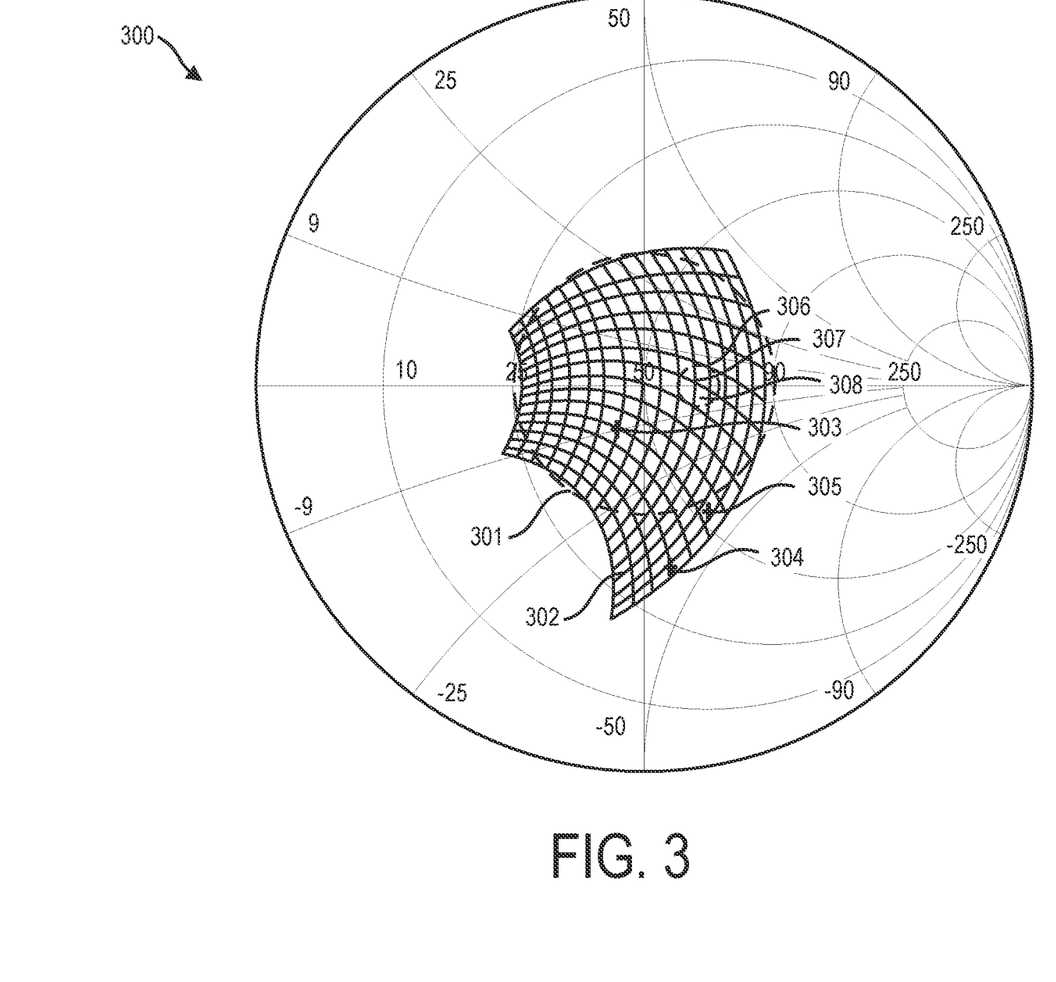
FIG. 3 is a Smith Chart which displays a tunable range for a hybrid matching network with a first-stage matching network with eight switch terminals. The tunable range illustrated in this Smith Chart corresponds to the hybrid matching network topology of FIG. 2.

FIG. 3 is a Smith Chart 300 which displays the tunable range 302 for the first stage of a hybrid matching network system that contains eight switch terminals 210 (see FIG. 2). The tunable range illustrated in this Smith Chart corresponds to the first-stage matching network of the hybrid matching network topology of FIG. 2. Notably, the Smith Chart 300 reflects the hybrid matching network 200 topology illustrated in FIG. 2 in which the first-stage matching network 201 has eight switch terminals 210. The tunable range 302 illustrated in FIG. 3 is the conjugate of the range of (e.g., load) impedances of which a first-stage matching network can transform to the target impedance (e.g. 50 ohms in this example).

In some implementations, the profile (e.g. shape) of the tunable range 301 can differ from this example. The profile of the tunable range 302 may be determined by the topology of the first-stage matching network and the value of the reactive tuning elements. In this example, the values of reactive tuning elements 221 in switch terminals 210, and the value of the reactive elements 213, 214, 216 in the impedance transformer 217 shown in FIG. 2 may determine the profile of the tunable range 302.

Most notably, because the first-stage matching network is a discrete system with a finite number of configurations, the number of switch terminals 210 (see FIG. 2) within the first-stage matching network of a hybrid matching network determines the density of the tunable range 302. Accordingly, the greater the number of switch terminals within the first-stage matching network, the greater the density of the resulting tunable range 302. In some implementations, eight switch terminals may be sufficient for applications that can tolerate a small amount of gamma at the input of the hybrid match system. As such, the number of switch terminals designed for a first-stage matching network may account for a target VSWR.

The tunable range 302 includes an impedance grid 306 of orthogonal arcs 307, 308. Each successive arc represents one increment in the total value of reactance in switch banks 205 and 206 (see FIG. 2) respectively. Load impedances that are the conjugate value of one of the intersections of 307 and 308 can be transformed to the target impedance precisely. Load impedances that fall in between these intersections, such as impedance point 305, can be very nearly transformed to the target impedance by choosing the switch configuration that most nearly represents the conjugate of that load impedance.

For example, an impedance point 303 within the tunable range 302 lies directly at the intersection of horizontal and vertical impedance arcs 307, 308. Accordingly, the first-stage matching network can tune this load impedance to match a source impedance with a high-degree of precision (e.g., 50+0.3j Ohms for a 50-Ohm source impedance). In contrast, the first-stage matching network can tune a load impedance point 305 to a source impedance with moderate-to-high precision (e.g., 50.5−2.4j Ohms).

In addition, the first-stage matching network of the hybrid matching network can tune a load impedance that is outside of a VSWR 301 but within the tunable range 302. For example, the load impedance represented by impedance point 304, which notably lies directly at the intersection of horizontal and vertical impedance arcs 307, 308, can be tuned directly to the source impedance with high-precision. Accordingly, the load impedance that is directly on arcs 307, 308 of the impedance grid 306 may be tuned directly to a source impedance regardless of the distance the load impedance is from the source impedance.

As previously discussed, the profile of the tunable range 302 may be determined by the total value of the reactive tuning elements 221 (see FIG. 2) in the switch terminals 210 and an impedance transformer. It may be advantageous to have the range of the first stage matching network skewed in one direction or another for specific applications where the direction of impedance shifts due to pulsing or other operational parameters of a plasma chamber or individual process are known and well characterized.

Figure 4:
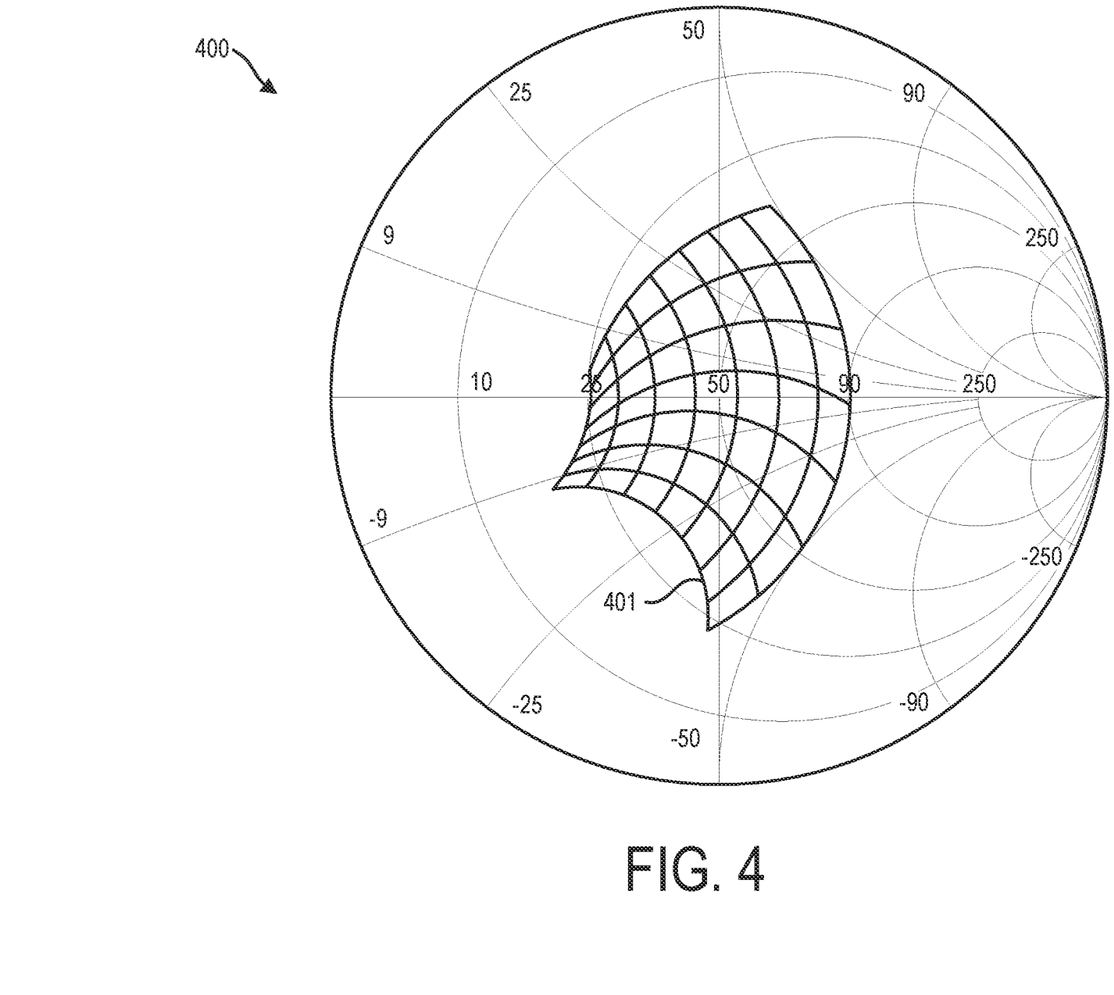
FIG. 4 is a Smith Chart which displays a tunable range for a hybrid matching network with a first-stage matching network with six switch terminals.
Figure 5:
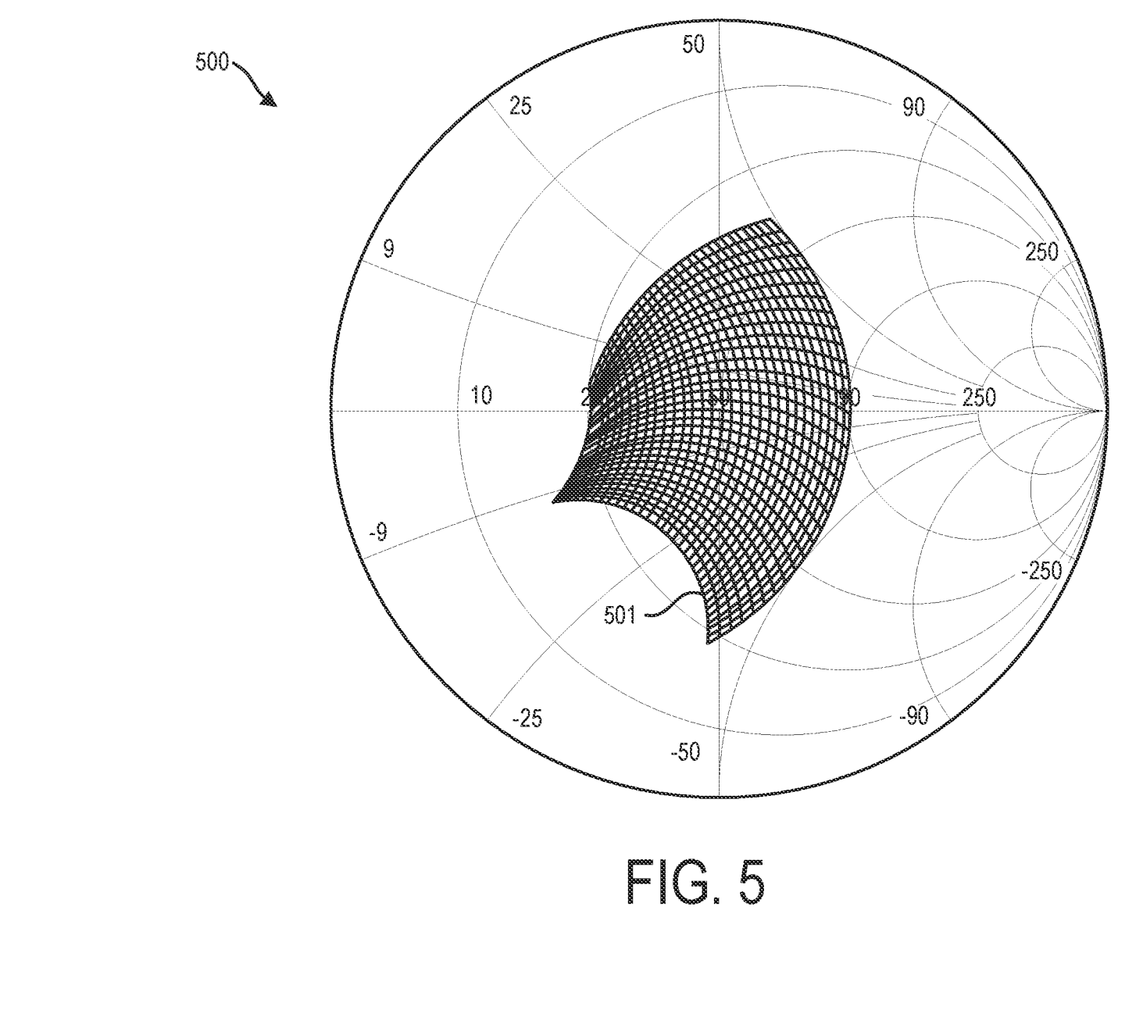
FIG. 5 is a Smith Chart which displays a tunable range for a hybrid matching network with a first-stage matching network with ten switch terminals.

FIG. 4 and FIG. 5 show the tunable range for two possible implementations of the first stage matching network. The difference between these two implementations is the number of switch terminals. In FIG. 4 the number of switch terminals is six, or three per bank, which yields tunable range 401. In FIG. 5 the number of switch terminals 210 is ten, or five per bank, which yields tunable range 501 on the Smith Chart 500. The gaps between discrete switch configurations are larger in FIG. 4 than FIG. 5; therefore, the worst-case impedance match can be less acute in a system with six switch terminals than a system with ten switch terminals.

Figure 6:
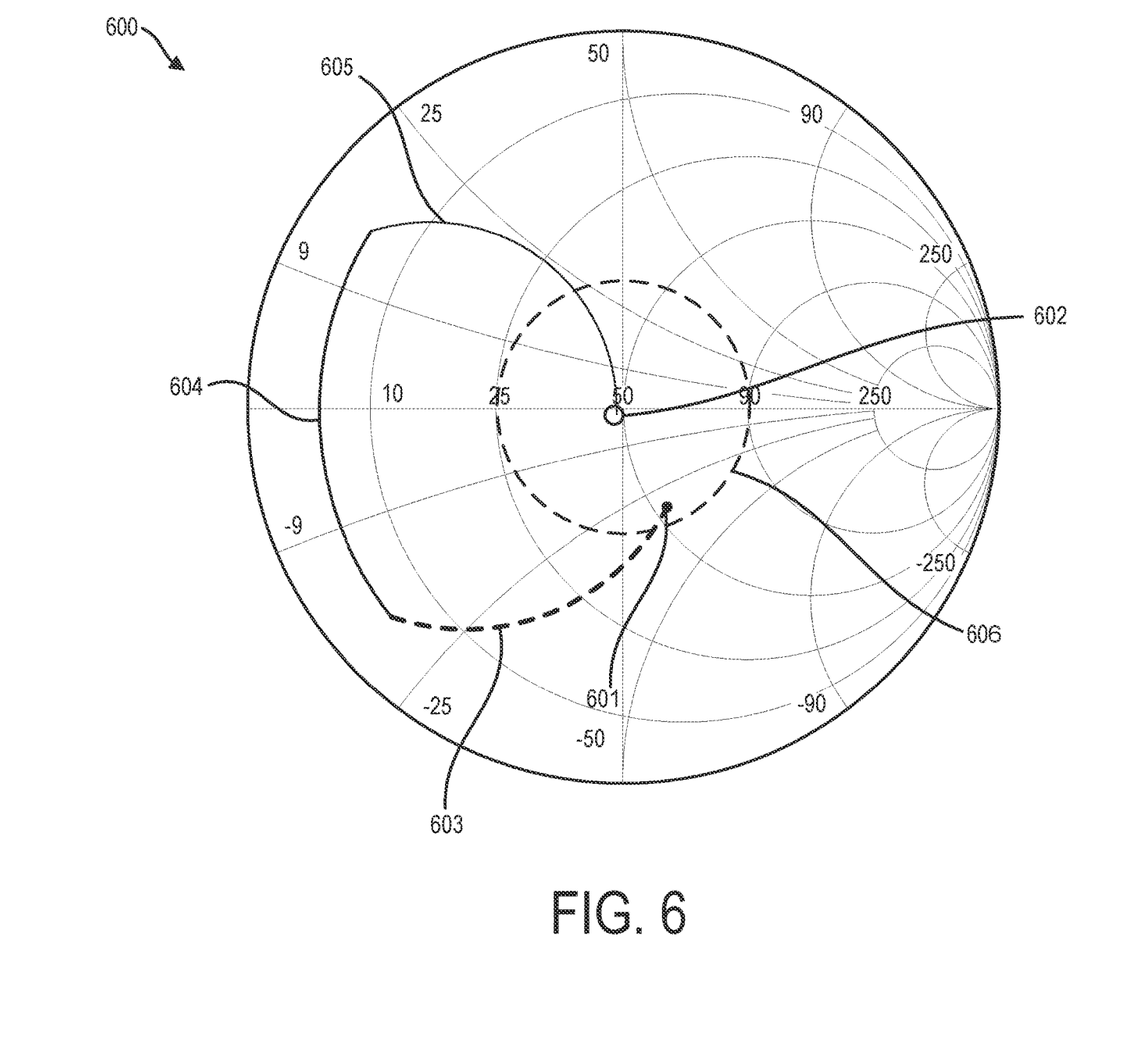
FIG. 6 is a Smith Chart illustrating an impedance transformation to tune a load impedance to a source impedance, according to a system and method of the present disclosure.

FIG. 6 is a Smith Chart 600 illustrating an impedance transformation to tune a load impedance of 53−j30 ohms (impedance point 601) to a target impedance (in this case, 50 ohms), according to a system and method of the present disclosure. In the example shown, a first-stage matching network of a hybrid matching network was employed to tune a load impedance to within a target VSWR 606 (e.g., to impedance point 602).

FIG. 6 further illustrates impedance curves 603-605 which represent the transformation of voltage and current in phase and magnitude through the first-stage matching component of the hybrid matching network. In the example shown, the impedance curve 603 is associated with a first bank of switches (e.g., on a first end of the impedance transformer) whereas the impedance curve 605 is associated with a second bank of switches (e.g., on a second end of the impedance transformer). Furthermore, the impedance curve 604 is associated with an inductor element of the impedance transformer. Collectively, curves 603-605 show a pathway in impedance transformation that the first-stage matching network undergoes to tune a load impedance to a target (e.g., source) impedance (e.g., impedance point 602) in a single step. As previously discussed, the first-stage matching network can tune a load impedance to a target impedance with high precision in various implementations. For example, impedance point 602 is close to 50 Ohms (e.g., 48.4−2.8j Ohms) for a target impedance of 50 Ohms.

Figure 7:
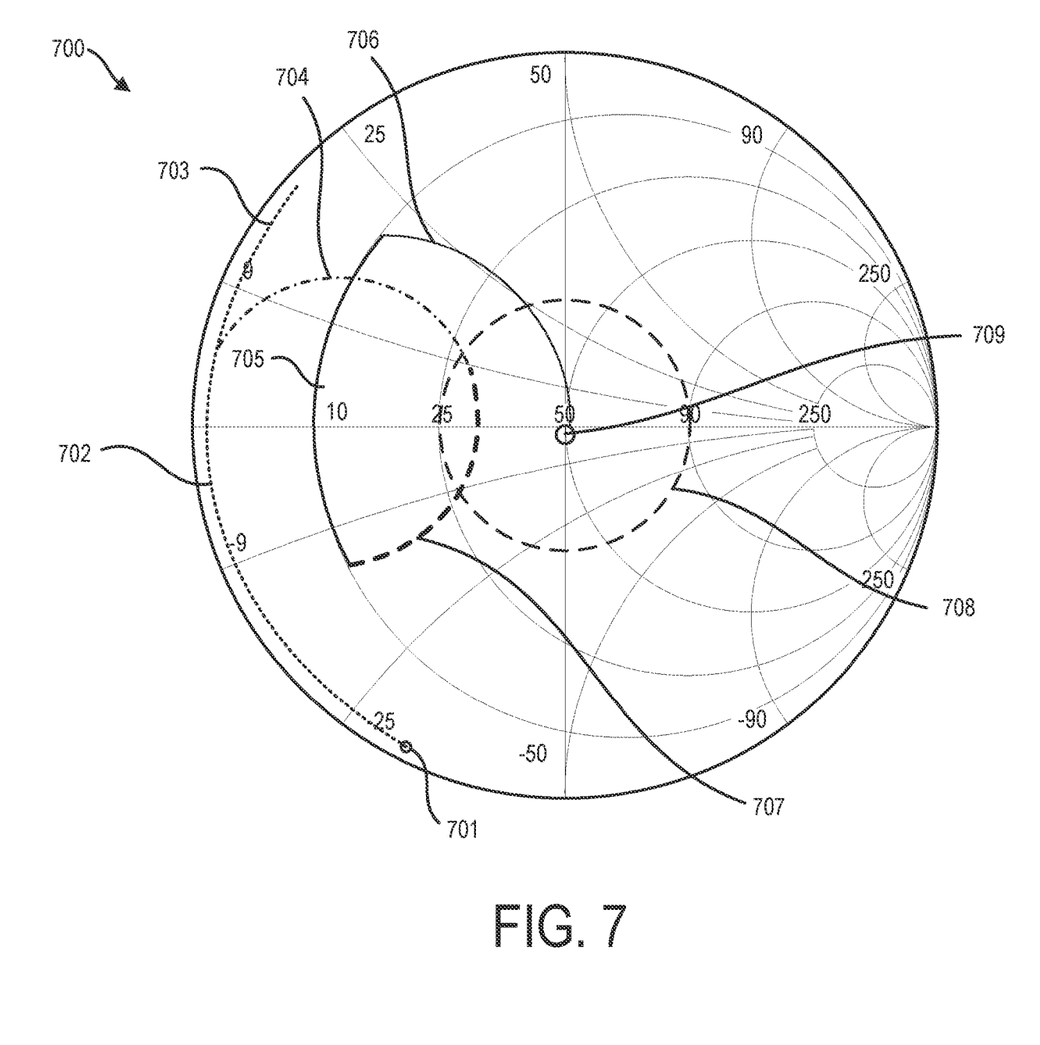
FIG. 7 is a Smith Chart illustrating an impedance transformation to match a load impedance to a target impedance, according to a system and method of the present disclosure.

FIG. 7 is a Smith Chart 700 illustrating an impedance transformation to match a load impedance 701 to a target impedance 709, according to a system and method of the present disclosure. This example is given to further demonstrate the advantages gained by using a hybrid matching network with the sensor arrangement as it is disclosed. Because the tuning goals of either stage network may be completely independent, both control loops may operate simultaneously without any unwanted interactions. In the example shown, a hybrid matching network was employed to tune a load impedance 701 of 1−j31 ohms to a target impedance 709 of 50 ohms. FIG. 7 depicts a Smith Chart 700 and impedance curves 702-707 which represent the path taken to transform the load impedance 701 to the target impedance 709 through the first and second-stage matching networks of the hybrid matching network.

In the example shown, the impedance curves 702-704 are associated with the impedance transformation attributed to the device elements of the second-stage matching network of a hybrid matching network. Similarly, the impedance curves 705-707 are associated with the impedance transformation attributed to the device elements of the first-stage matching network of a hybrid matching network. For example, the impedance curves 705-707 are associated with the impedance transformation attributed to capacitors within a first bank of switch terminals (i.e., curve 707), an inductor device element of the impedance transformer (i.e., curve 705), and the capacitors within a second bank of switch terminals (i.e., curve 706) of the first-stage matching network of the hybrid matching network. This example uses the topologies chosen in FIG. 2, where the first-stage matching network 201 (see FIG. 2) is a pi network with two banks 205, 206 of switch terminals 210 and the second-stage matching network 202 (see FIG. 2) is a step-down L network which includes a variable shunt capacitor, a variable series capacitor, and a fixed series inductor. It should be obvious to a person having ordinary skill in the art having the benefit of this disclosure that this hybrid matching system could employ alternative network topologies for the first-stage matching network and the second-stage matching network, so long as doing so does not depart from the spirit and scope of the present disclosure.

In the example, the load impedance 701 of 1−31j is transformed by the second-stage matching network to 28.4+8.2j. When the sensor 203 (see FIG. 2) calculates an impedance within the tunable range of the first-stage matching network, the first-stage matching network may become active. The switches 212 (see FIG. 2) may be actuated to the configuration that most nearly matches the conjugate of the calculated load impedance. From the moment that the switches 212 (see FIG. 2) are correctly actuated, the reflection coefficient at the input of the system may be minimized. The second-stage matching network may continue to drive to minimize the reflection coefficient at its input 215 (see FIG. 2). As the impedance looking into node 215 (see FIG. 2) changes by the motion of the tunable elements and the load presented by the plasma chamber, the first-stage matching network may still be active, provided the impedance looking into node 215 (see FIG. 2) is still within its tunable range. Even as those operations continue, from the overall system perspective, the tuning goal has already been achieved.

Still referring to FIG. 7, the impedance curve 707 is associated with a first bank of switches (e.g., on a first end of the impedance transformer) whereas the impedance curve 706 is associated with a second bank of switches (e.g., on a second end of the impedance transformer). Furthermore, the impedance curve 705 is associated with an inductor element of the impedance transformer. Collectively, curves 705-707 show a pathway in impedance transformation that the first-stage matching network undergoes to tune a load impedance to a target (e.g., source) impedance (e.g., impedance point 709). As previously discussed, the first-stage matching network can tune a load impedance to a target impedance with high precision in various implementations. For example, impedance point 709 is close to 50 Ohms (e.g., 50.2–0.4j Ohms) for a target impedance of 50 Ohms.

Figure 8:
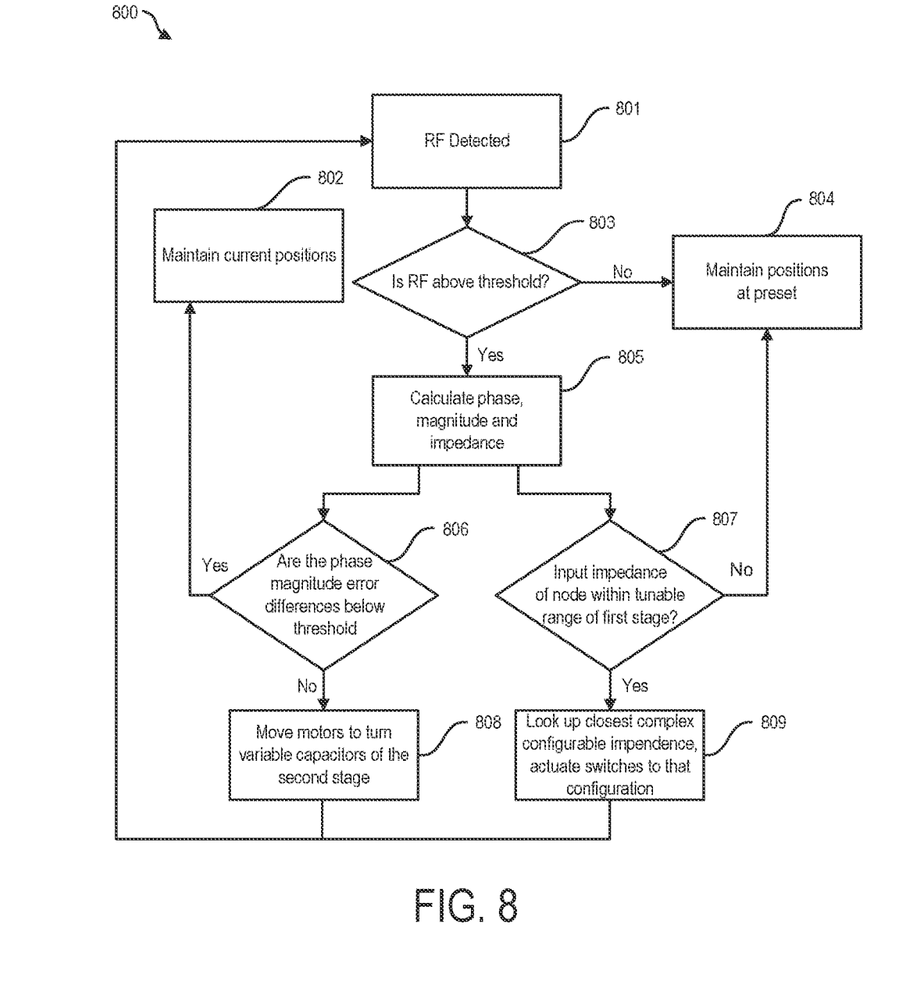
FIG. 8 is a flowchart of a method to perform impedance matching, according to a system and method of the present disclosure.

FIG. 8 is a flowchart 800 of a method to perform impedance matching according to a system and method of the present disclosure. Flowchart 800 begins with detecting a RF signal (block 801). The RF signal may be detected by a sensor element, a component of the hybrid matching network. If the detected RF signal is greater in amplitude than a pre-determined threshold which is defined according to an application, the sensor performs calculations (e.g., phase error, magnitude error, and impedance) necessary to begin the tuning procedure (block 805). If the amplitude of the phase and magnitude error is not higher than the pre-determined threshold, and the calculated impedance is not inside the tunable range of the first-stage matching network, then both stages maintain their pre-set positions (block 802, 804). These pre-set positions are application dependent and can exist anywhere within the usable range of the tunable elements in the network.

In addition, if the error signals generated by comparing the magnitudes and phase relationship of voltage and current are above some threshold, then they can be used to tune the variable elements in the second-stage matching network (block 808). If the input impedance at node 215 (see FIG. 2), calculated from the difference in magnitude and phase relationship of voltage and current, is within the tunable range of the first-stage (block 807) then the switch terminals can be actuated to the configuration that causes the output impedance of the first-stage to match the complex conjugate of the calculated load impedance (block 809). If the phase and magnitude derived error signals are smaller than some threshold, while RF is detected at a sufficient level, the tunable elements in the second-stage matching network can remain at their current position as the tuning goal has been achieved (block 802). The first-stage matching network can continuously monitor the calculated input impedance to node and change its configuration to minimize the reflection coefficient seen at its input.

Although the present disclosure has been described in detail, it should be understood by a person having ordinary skill in the art, with the benefit of this disclosure, that various changes, substitutions and alterations can be made without departing from the spirit and scope of the disclosure. Any use of the words "or" and "and" in respect to features of the disclosure indicates that examples can contain any combination of the listed features, as is appropriate given the context.

While illustrative implementations of the application have been described in detail herein, it is to be understood that the inventive concepts may be otherwise variously embodied and employed, and that the appended claims are intended to be construed to include such variations, except as limited by the prior art.

Reference throughout this specification to "one implementation" or "an implementation" means that a particular feature, structure, or characteristic described in connection with the implementation is included in at least one implementation of the present disclosure. Thus, the appearances of the phrases "in one implementation" or "in some implementations" in various places throughout this specification are not necessarily all referring to the same implementation. Furthermore, the particular features, structures, or characteristics may be combined in any suitable manner in one or more implementations.

In the foregoing specification, a detailed description has been given with reference to specific exemplary implementations. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
   determining a presence of RF waves that exceeds a first pre-determined threshold;
   calculating a first value representing a magnitude and phase relationship of voltage and current;
   based on the first value, tuning a second-stage matching network of a hybrid matching network;
   calculating a second value representing an impedance from the calculated magnitude and phase relationship of the voltage and current; and
   based on the second value, tuning a first-stage matching network of the hybrid matching network.

2. The method of claim 1, further comprising allowing for the simultaneous execution of parallel control loops, the parallel control loops being associated with the first-stage matching network and the second-stage matching network, which simultaneous execution directs the first-stage matching network and the second-stage matching network of the hybrid matching network to achieve shorter system tuning times.

3. The method of claim 1, wherein, when the first-stage matching network is disengaged, the first-stage matching network functions as a filter.

4. The method of claim 1, further comprising configuring a state of a plurality of switch terminals within the first-stage matching network as part of engaging the first-stage matching network.

5. The method of claim 1, wherein the first-stage matching network is engaged when an input impedance to the second-stage matching network enters a tunable range of the first-stage matching network.

6. The method of claim 1, wherein operation of the first-stage matching network and the second-stage matching network occurs either independently, simultaneously, or sequentially.

7. The method of claim 1, wherein the tuning of the second stage matching network is offset relative to a characteristic impedance of a system in order to optimize a secondary tuning goal.

8. The method of claim 7, wherein the secondary tuning goal is to minimize a transformation Q of the first stage matching network.

9. The method of claim 7, wherein the secondary tuning goal is to increase or decrease the Q of an entire hybrid matching system.

10. The method of claim 7, wherein the secondary tuning goal is to maximize a usable tuning range of the first stage matching network.

11. A method, comprising:
determining a presence of a plurality of radio frequency (RF) waves that exceed a first pre-determined threshold;
calculating a first value representing a magnitude and phase relationship of forward power and reflected power;
based on the first value, tuning a second-stage matching network of a hybrid matching network;
calculating a second value representing an impedance from the calculated magnitude and phase relationship of the forward power and the reflected power; and
based on the second value, tuning a first-stage matching network of the hybrid matching network.

12. The method of claim 11, further comprising allowing for the simultaneous execution of parallel control loops, the parallel control loops being associated with the first-stage matching network and the second-stage matching network, which simultaneous execution directs the first-stage matching network and the second-stage matching network of the hybrid matching network to achieve shorter system tuning times.

13. The method of claim 11, wherein, when the first-stage matching network is disengaged, the first-stage matching network functions as a filter.

14. The method of claim 11, further comprising configuring a state of a plurality of switch terminals within the first-stage matching network as part of engaging the first-stage matching network.

15. The method of claim 11, wherein the first-stage matching network is engaged when an input impedance to the second-stage matching network enters a tunable range of the first-stage matching network.

16. The method of claim 11, wherein operation of the first-stage matching network and the second-stage matching network occurs either independently, simultaneously, or sequentially.

17. The method of claim 11, wherein tuning of the second stage matching network is offset relative to a characteristic impedance of a system in order to optimize a secondary tuning goal.

18. The method of claim 17, wherein the secondary tuning goal is to minimize a transformation Q of the first stage matching network.

19. The method of claim 17, wherein the secondary tuning goal is to increase or decrease the Q of an entire hybrid matching system.

20. The method of claim 17, wherein the secondary tuning goal is to maximize a usable tuning range of the first stage matching network.

* * * * *